United States Patent [19]
Garibaldi et al.

[11] 4,003,937
[45] Jan. 18, 1977

[54] METHOD FOR THE PREPARATION OF YTTERBIUM(III) BETA-DIKETONATES

[75] Inventors: Pierpaolo Garibaldi, San Donato Milanese; Fausto Calderazzo, Ghezzano, both of Italy

[73] Assignee: Sham Progretti S.p.A., San Donato Milanese, Italy

[22] Filed: Dec. 10, 1975

[21] Appl. No.: 639,445

[30] Foreign Application Priority Data
Dec. 10, 1974  Italy ............................ 30337/74

[52] U.S. Cl. ......................... 260/429.2; 260/429 J
[51] Int. Cl.² ........................................ C07F 5/00
[58] Field of Search ................................ 260/429.2

[56] References Cited
UNITED STATES PATENTS 3,631,081  12/1971  Huggins et al. ............ 260/429.2 X

*Primary Examiner*—Leland A. Sebastian
*Attorney, Agent, or Firm*—Ralph M. Watson

[57] ABSTRACT

A method is disclosed for the preparation of ytterbium-(III) beta-diketonates, the improvement consisting in that the reaction between an ytterbium(III) halide and a chelating agent (such as acetylacetone, dibenzoylmethane and dipivaloylmethane for example) is caused to take place in an anhydrous medium and in the presence of gaseous ammonia, the ytterbium(III) halide being also anhydrous.

6 Claims, No Drawings

METHOD FOR THE PREPARATION OF YTTERBIUM(III) BETA-DIKETONATES

This invention relates to a method for the preparation of ytterbium(III) beta-diketonates starting from ytterbium halides in the presence of gaseous ammonia.

The synthesis of ytterbium(III) beta-diketonates by treatment of beta-diketones with alcoholic or aqueous solutions of the halides is known. However, the ytterbium halide, as dissolved either in water or alcohol, can undergo hydrolysis reactions and still retain water or alcohol molecules of coordination, which reduce the solubility of the chelates in hydrocarbon solutions. The applicants have now found a simple method for the synthesis of ytterbium(III) beta-diketonates starting from anhydrous ytterbium halides (dehydrated with thionyl chloride) which are treated with the chelating agent in the presence of a nonaqueous solvent and gaseous ammonia.

The reaction takes place according to the following pattern:

$$YbX_3 + 3 BH + 3 NH_3 \rightarrow 3 NH_4Cl + YbB_3$$

wherein X is the halogenide ion, BH the chelating agent selected from acetyl-acetone (AcacH), dibenzoylmethane (DBMH, dipivaloylmethane (DPMH).

The reaction evolves towards the formation of the end products in a complete way, no products other than those reported being detected. The reaction is carried out in the presence of an anhydrous solvent selected from tetrahydrofuran, ethers, ketones, esters, at a temperature comprised between 20° C and 60° C. The method of the present invention enables the synthesis of chemically pure beta-diketonates to be arrived at without resorting to any particular crystallization and/or sublimation procedures.

On completion of the reaction, the reaction mixture is filtered and separated from the ammonium chloride, the latter being washed way with tetrahydrofuran. The amount of NH$_4$Cl has been found to be 98 % of theory. The filtered solution is partially evaporated under reduced pressures and the precipitation of the ytterbium compound is facilitated by the addition of heptane. There are obtained 4.26 grams of the complex, with a yield of about 95 %.

The table reports the data relating to the complex and those for other derivatives as obtained in a similar way.

TABLE 1

(XX) PROPERTIES OF THE COMPLEX YTTERBIUM(III) BETA-DIKETONATES

| (Reaction temperature: Room temperature) | | | | |
|---|---|---|---|---|
| | Formula | Mol.wt. | Color | Yield % (°) |
| Yb(Acac)$_3$ | C$_{15}$H$_{21}$O$_6$Yb | 464.3 | white | 92 |
| Yb(DBM)$_3$ | C$_{45}$H$_{33}$O$_6$Yb | 842.8 | yellow | 95 |
| Yb(DPM)$_3$ | C$_{33}$H$_{57}$O$_6$Yb | 722.8 | yellow | 92 |

(°) Yield of analytically pure product. At least three elements have been analyzed for each compound. The products did not contain nitrogen.
(XX) Solvent used: tetrahydrofuran.

What we claim is:

1. A method for the preparation of ytterbium (III) beta-diketonates comprising of reacting an anhydrous ytterbium (III) halide with a chelating agent selected from the group consisting of acetylacetone, dibenzoylmethane and dipivaloylmethane in the presence of gaseous ammonia and of a nonaqueous solvent.

2. A method for the preparation of ytterbium (III) chelates according to claim 1 characterized in that the nonaqueous solvent is selected from tetrahydrofuran, ethers, ketones and esters.

3. A method for the preparation of ytterbium (III) chelates as defined in claim 1 wherein the reaction is carried out at a temperature in the range from 20° C to 60° C.

4. A method for the preparation of ytterbium (III) chelates as defined in claim 1 wherein the chelating agent is acetylacetone.

5. A method for the preparation of ytterbium (III) chelates as defined in claim 1 wherein the chelating agent is dibenzoylmethane.

6. A method for the preparation of ytterbium (III) chelates as defined in claim 1 wherein the chelating agent is dipivaloylmethane.

* * * * *

UNITED STATES PATENT AND TRADEMARK OFFICE
CERTIFICATE OF CORRECTION

PATENT NO. : 4,003,937
DATED : January 18, 1977
INVENTOR(S) : Pierpaolo Garibaldi and Fausto Calderazzo It is certified that error appears in the above-identified patent and that said Letters Patent are hereby corrected as shown below:

First page, correct line "[73]" to read:

--[73] Assignee: Snamprogetti S.p.A., San Donato Milanese, Italy --.

Signed and Sealed this

Seventh Day of June 1977

[SEAL]

Attest:

RUTH C. MASON
Attesting Officer

C. MARSHALL DANN
Commissioner of Patents and Trademarks